US00PP28929P2

(12) United States Plant Patent
Lim

(10) Patent No.: US PP28,929 P2
(45) Date of Patent: Feb. 6, 2018

(54) ***ROSA* PLANT NAMED 'LIMKISS'**

(50) Latin Name: *Rosa hybrida*
Varietal Denomination: LIMkiss

(71) Applicant: Peter Ping Lim, Escondido, CA (US)

(72) Inventor: Peter Ping Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,569

(22) Filed: Oct. 13, 2016

(51) Int. Cl.
*A01H 5/02* (2006.01)

(52) U.S. Cl.
USPC ..... Plt./137

(58) Field of Classification Search
USPC ..... Plt./137
See application file for complete search history.

*Primary Examiner* — Annette H Para
(74) *Attorney, Agent, or Firm* — Cassandra Bright

(57) ABSTRACT

A new and distinct *Rosa* cultivar named 'LimKiss' is disclosed, characterized by a vigorous, climbing plant habit and flowers colored deep magenta. Flowers have a strong, spicy scent. Plants can be grown on their own roots and are strongly resistant to black spot. The new variety is a *Rosa*, normally produced as an outdoor garden or container plant.

1 Drawing Sheet

Latin name of the genus and species: *Rosa hybrida.*
Variety denomination: 'LIMkiss'.

BACKGROUND OF THE INVENTION

The new *Rosa* cultivar is a product of a planned breeding program conducted by the inventor, Peter Ping Lim. The objective of the breeding program was to produce vigorous new garden rose varieties for ornamental commercial applications. The cross resulting in this new variety was made between April and June 2010.

The seed parent is the unpatented variety *Rosa* 'Ebb Tide'. The pollen parent is the unpatented variety *Rosa* 'Golden Eye'. The new variety was selected in June of 2011 by the inventor in a group of seedlings resulting from the 2010 crossing in a research nursery in McMinnville, Oreg.

Asexual reproduction of the new cultivar was performed by vegetative cuttings. This was first performed at a research greenhouse in McMinnville, Oreg. in June 2011 and has shown that the unique features of this cultivar are stable and reproduced true to type in more than 5 successive generations.

SUMMARY OF THE INVENTION

The cultivar 'LIMkiss' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMkiss' These characteristics in combination distinguish 'LIMkiss' as a new and distinct *Rosa* cultivar:

1. Double flowering tea rose with a vigorous plant habit.
2. Climbing plant habit.
3. Continuing flowering double hybrid tea flower.
4. Deep magenta coloration.
5. Strong spicy fragrance.

6. Can be grown without grafting, performs vigorously on its own roots.
7. Easy to propagate and root.
8. Resistance to black spot disease.

Plants of the new cultivar 'LIMkiss' are similar to plants of the seed parent, in most horticultural characteristics, however, plants of the new cultivar 'LIMkiss' differ in the following:

1. The new variety has a climbing habit, the seed parent does not.
2. The new variety has a magenta colored flower, the seed parent has a purple flower.

Plants of the new cultivar 'LIMkiss' are similar to plants of the pollen parent in most horticultural characteristics, however, plants of the new cultivar 'LIMkiss' differ in the following;

1. The pollen parent has red colored flowers, the new variety has magenta flowers.
2. The new variety has a double flower, the pollen parent has a single flower.

COMMERCIAL COMPARISON

Plants of the new cultivar 'LIMkiss' can also be compared to the commercial variety *Rosa* 'William Buffin', unpatented. These varieties are similar in most horticultural characteristics, however 'LIMkiss' differs in the following:

1. The new variety has a larger flower than this comparator.
2. The new variety is more fragrant than this comparator.
3. The new variety is less heat and drought resistant than this comparator.

Plants of the new cultivar 'LIMkiss' can also be compared to the commercial variety *Rosa* 'Tabone', U.S. Plant Pat. No. 5,633. These varieties are similar in most horticultural characteristics, however 'LIMkiss' differs in the following:

1. The new variety has a climbing plant habit, this comparator does not.

2. The new variety produces more branches than this comparator.
3. The new variety is more disease resistant than this comparator.
4. The new variety has a stronger fragrance than 'Tabone'.

BRIEF DESCRIPTION OF THE PHOTOGRAPH

The accompanying photograph in FIG. 1 illustrates in full color a close up of an individual flower. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LIMkiss' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'LIMkiss'.

*Market category*.—Climbing garden rose.

PROPAGATION

Time to initiate roots: About 15 days at approximately 20° C.

Time to produce a rooted cutting: About 35 days at approximately 20° C.

PLANT

Age of plant described: Approximately 2 years.
Growth habit: Climbing.
Container size: 2 gallon.
Height: 122 cm.
Plant spread: 65 cm.
Rootstock: Own root.
Growth rate: Rapid.
Branching characteristics: Sympodial branching.
Length of primary lateral branches: Approximately 60 to 100 cm.
Diameter of lateral branches: Approximately 1.1 cm.
Quantity of lateral branches: 6 to 8 main lateral branches.
Branches:
Young wood:
*Diameter*.—Approximately 0.7 cm.
*Texture*.—Glabrous, sparse thorns.
*Approximately density/quantity of thorns*.—Less than 1 per square cm.
*Color*.—Near Green 143C.
Branches:
Old wood:
*Diameter*.—Approximately 1.1 cm, after 2 years.
*Color*.—Near Green 143B.
*Texture*.—Slightly rough with moderate quantity of woody striations.
Thorns:
*Approximately density/quantity of thorns*.—Approximately 1 per square cm.
*Color of thorns*.—Immature: Red 39A. Mature: Near Greyed-Yellow 162A.
*Shape*.—Deltoid, moderately hooked.
*Height*.—Average 1.1 cm.
*Diameter*.—Base near 1.2 cm. Tip near 0.2 cm.

FOLIAGE

Leaf:
*Arrangement*.—Alternate and compound.
*Quantity*.—Approximately 18 per main branch.
*Internode*.—Average range 3.5 to 9 cm.
*Average length*.—Approximately 11 cm.
*Average width*.—Approximately 8.5 cm.
Rachis:
*Average length*.—Approximately 6.2 cm.
*Average diameter*.—Approximately 0.2 cm.
*Color*.—Near RHS Green 143C.
Leaflet:
*Quantity*.—3 or 5 per leaf.
*Average length*.—Approximately 4.7 cm.
*Average width*.—Approximately 3.5 cm.
*Shape of blade*.—Ovate.
*Apex*.—Sharply acute.
*Base*.—Rounded.
*Margin*.—Serrated, somewhat sharp.
*Texture of top surface*.—Semi glossy.
*Texture of bottom surface*.—Matte.
*Appearance of top surface*.—Semi glossy.
*Appearance of bottom surface*.—Matte.
*Texture of top surface*.—Glabrous.
*Texture of bottom surface*.—Glabrous.
*Color*.—Young foliage upper side: Near Green 137A. Young foliage under side: Near Green 138A. Mature foliage upper side: Darker than Green 137A. Mature foliage under side: Near Green 137D.
*Venation*.—Type: Reticulate. Venation color upper side: Near Yellow-Green 144A. Venation color under side: Near Yellow-Green 144C.
Petiole:
*Average length*.—Approximately 2.0 cm.
*Average diameter*.—Approximately 0.3 cm.
*Color*.—Near Green 143C.
*Texture*.—Glabrous.

FLOWER

Natural flowering season: Spring until Autumn.
Inflorescence type and habit: Raceme.
Rate of flower opening: Approximately 7 days from bud to fully opened flower.
Flower longevity on plant: 7 days, after fully opened.
Quantity of flowers: 2 to 4.
Inflorescence size:
*Diameter*.—Approximately 14 cm.
*Height*.—Approximately 12 cm.
Peduncle:
*Length*.—2 cm.
*Diameter*.—0.4 cm.
*Color*.—Near RHS Green 143C.
Petals:
*Petal arrangement*.—Multiple rotate, overlapping whorls.

*Petal quantity.*—20 to 30.
*Length.*—4.5 cm.
*Width.*—4.0 cm.
*Shape.*—Broad delate to cordate.
*Margin.*—Entire, slightly curved down.
*Apex.*—Rounded to shallowly lobed.
*Base.*—Broad attenuate.
*Texture.*—Glabrous all surfaces.

Color:

*Petals.*—When opening: Upper surface: Upper section near Red-Purple N66C, center section near 70C, base near 69D. Lower surface: Upper section near Red-Purple N66C, center section near 70C, base near 69D. Strong mid vein White 155A. Fully opened: Upper surface: Upper section near Red-Purple 67A, center section near 67C, base near White 155A. Lower surface: Upper section near Red-Purple 67B, center section near 67C, base near White 155A. Color Changes when aging, both surfaces: Upper section near Red-Purple 70A, center section near 70C, base near White 155A.

Bud:

*Shape.*—Round.
*Length.*—Approximately 2.5 cm.
*Diameter.*—Approximately 1.7 cm.
*Color.*—Near Red-Purple 60B.

Sepals:

*Quantity.*—5.
*Length.*—1.8 cm.
*Width.*—0.8 cm.
*Shape.*—Narrow deltoid.
*Apex.*—Acuminate.
*Margin.*—Entire, occasionally long awn-like structures emerge from sides.
*Color.*—Interior Surface: Near Green RHS 138A. Exterior Surface: Near Green RHS 143C.
*Texture.*—Densely pubescent upper and lower surfaces.

Receptacle:

*Length.*—1.1 cm.
*Width.*—0.7 cm.
*Shape.*—Conical.
*Color.*—Near RHS Green 143C.

Fragrance: Very strong, spicy rose fragrance.

REPRODUCTIVE ORGANS

Stamens:

*Quantity.*—Average range 50 to 70.
*Filament length.*—Approximately 0.7 to 1.1 cm.
*Filament color.*—Near Red 36D.

Anthers:

*Length.*—0.2 cm.
*Shape.*—Linear.
*Color.*—Near Red 55A.
*Pollen.*—Color: Greyed-Orange N170D. Quantity: Scant.

Pistil:

*Number.*—Approximately 30.
*Pistil length.*—Approximately 1.2 cm.
*Style.*—Length: Approximately 0.4 cm. Color: Near Green-Yellow 1D.
*Stigma.*—Shape: Linear. Color: Near Yellow 10C.
*Ovary color.*—Near RHS White 155C.
*Ovary shape.*—Oblong.
*Ovary length.*—Average 0.5 cm.
*Ovary diameter.*—Average 0.2 cm.

OTHER CHARACTERISTICS

Seeds and fruits: Not observed.

Disease/pest resistance: Good overall disease resistance to normal pests and diseases typical of garden roses.

What is claimed is:

1. A new and distinct hybrid tea cultivar of *Rosa* plant named 'LIMkiss' as herein illustrated and described.

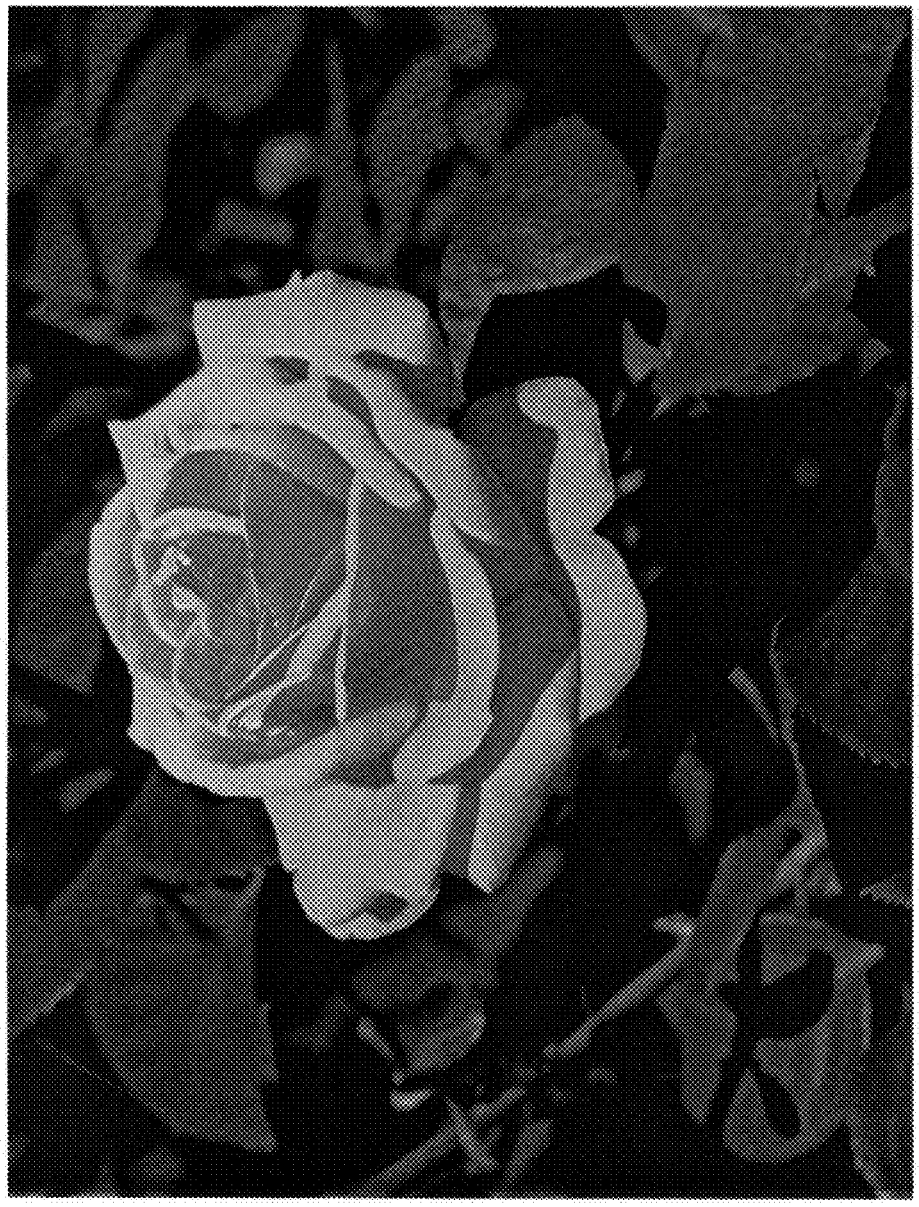

* * * * *